United States Patent
Pape et al.

(10) Patent No.: US 8,791,302 B2
(45) Date of Patent: Jul. 29, 2014

(54) PROCESS FOR PREPARING AN N,N-DIALKY-ETHANOLAMINE HAVING HIGH COLOR STABILITY

(75) Inventors: Frank-Friedrich Pape, Kleinniedesheim (DE); Johann-Peter Melder, Böhl-Iggelheim (DE); Alfred Krause, Speyer (DE); Roland Bou Chedid, Mannheim (DE); Martin Rudloff, Gönnheim (DE)

(73) Assignee: BASF SE, Ludwigshafen (DE)

( * ) Notice: Subject to any disclaimer, the term of this patent is extended or adjusted under 35 U.S.C. 154(b) by 180 days.

(21) Appl. No.: 13/328,230

(22) Filed: Dec. 16, 2011

(65) Prior Publication Data

US 2012/0157715 A1 Jun. 21, 2012

Related U.S. Application Data

(60) Provisional application No. 61/424,081, filed on Dec. 17, 2010.

(51) Int. Cl.
*C07C 213/00* (2006.01)

(52) U.S. Cl.
USPC .......................................................... 564/478

(58) Field of Classification Search
USPC .................................. 564/301, 478
See application file for complete search history.

(56) References Cited

U.S. PATENT DOCUMENTS

| | | | |
|---|---|---|---|
| 2,337,004 A | 12/1943 | Schwoegler et al. | |
| 2,373,199 A | 4/1945 | Schwoegler et al. | |
| 2,823,236 A | 2/1958 | Lowe et al. | |
| 3,131,132 A | 4/1964 | Moss et al. | |
| 3,567,779 A | 3/1971 | Currier et al. | |
| 5,663,444 A | 9/1997 | Melder et al. | |
| 6,774,264 B2 | 8/2004 | Delanghe et al. | |
| 2004/0068143 A1* | 4/2004 | Garg et al. | 564/503 |
| 2011/0257437 A1 | 10/2011 | Melder et al. | |

FOREIGN PATENT DOCUMENTS

| | | |
|---|---|---|
| DE | 1 004 620 B | 3/1957 |
| DE | 23 57 076 A1 | 5/1975 |
| DE | 30 40 732 A1 | 5/1981 |
| DE | 203 534 A1 | 10/1983 |
| DE | 44 14 879 A1 | 11/1995 |
| EP | 28 555 A1 | 5/1981 |
| EP | 70 978 A1 | 2/1983 |
| EP | 752 412 A1 | 1/1997 |
| GB | 1479747 A | 7/1977 |
| GB | 2061939 A | 5/1981 |
| JP | 57021351 A | 2/1982 |
| JP | 61186349 A | 8/1986 |
| JP | 01157938 A | 6/1989 |
| JP | 01160947 A | 6/1989 |
| WO | WO-2010/069856 | 6/2010 |
| WO | WO-2011/082967 | 7/2011 |

OTHER PUBLICATIONS

H.L. Sanders et al., "Ethoxylation of Fatty Acids", J. Am. Oil Chemists' Soc. 46, (1969), pp. 167-170.

E. Tobler et al., "Die Reaktion von 1,2-Epoxy-octan mit 2-Dimethylamino-äthanol", Helv. Chim Acta 52, (1969), pp. 408-418.

International Search Report of PCT/EP2011/072936 mailed Mar. 16, 2012.

* cited by examiner

*Primary Examiner* — Yong Chu
*Assistant Examiner* — Sonya Wright
(74) *Attorney, Agent, or Firm* — Drinker Biddle & Reath LLP

(57) ABSTRACT

A process for preparing an N,N-dialkylethanolamine of the formula I having high color stability

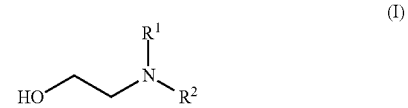

where $R^1$ and $R^2$ are each independently a $C_1$- to $C_8$-alkyl group, by reacting ethylene oxide (EO) with a corresponding dialkylamine ($R^1R^2NH$) in the presence of water, wherein the reaction is effected continuously in a reactor, the reaction temperature is in the range from 90 to 180° C. and the residence time (RT) in the reactor is in the range from 1 to 7 min, the reactor output is treated thermally at a temperature in the range from 80 to 160° C. over a period in the range from 20 to 1000 min, and then the N,N-dialkylethanolamine is removed by distillation.

18 Claims, No Drawings

PROCESS FOR PREPARING AN N,N-DIALKY-ETHANOLAMINE HAVING HIGH COLOR STABILITY

CROSS-REFERENCE TO RELATED APLLICATIONS

This application claims the benefit of U.S. Provisional Application 61/424,081, filed Dec. 17, 2010, which is incorporated by reference.

BACKGROUND OF THE INVENTION

The present invention relates to a process for preparing an N,N-dialkylethanolamine having high color stability.

N,N-dialkylethanolamines are important intermediates for the chemical and pharmaceutical industry. Dimethylethanolamine finds use in a wide variety of different fields, for example in the form of salts, soaps, ethers and esters, as an emulsifier and surface-active substance and as a catalyst in polyurethane chemistry. In the pharmaceutical industry, it is used to synthesize active ingredients (tranquilizers, antihistamines and analgesics). Discoloration in N,N-dialkylethanolamines, such as dimethylethanolamine, is undesirable in most applications.

The addition of almost all amines onto ethylene oxide (EO) is, like that of ammonia, accelerated considerably by addition of water. For instance, heating to 150° C. for several hours is necessary for reaction of EO with dimethylamine (DMA); in contrast, the reaction proceeds even under cold conditions when an aqueous DMA solution is used. An effect similar to water is also possessed by alcohols such as methanol or ethanol (Houben Weyl, Methoden der organischen Chemie [Methods of Organic Chemistry], Volume 11/1, 1957, page 311 ff.).

It is known that alkanolamines react further as a result of ethoxylation of the hydroxyl group to give more highly ethoxylated products. This further reaction can be substantially suppressed by use of excess amine (1.1:1 to 4:1) (DE 23 57 076 A, DD 203 534 A (VEB Synthesewerk Schwarzheide), U.S. Pat. Nos. 2,337,004 A, 2,373,199 A).

It is also known that tertiary amines, for example dimethylethanolamine (DMEOA), react both in the absence and in the presence of water below 80° C. with oxiranes to give thermally labile quaternary ammonium compounds which decompose more or less rapidly above 90° C. (E. Tobler et al., Helv. Chim Acta 52, 1969, page 408-418). The formation of these bases is disadvantageous in several ways:

1) Fixing of EO in the quaternary bases leads to selectivity losses.

2) Due to their high basicity, the quaternary bases catalyze the formation of more highly ethoxylated compounds. Dodecylamine undergoes addition, for example, of 2 mol of EO above 200° C. (→no quaternary bases exist) and of 10 mol of EO below 90° C. (→quaternary bases exist) to give more highly ethoxylated compounds (H. L. Sanders et al., J. Am. Oil Chemists' Soc. 46, page 167-170). The overall result is selectivity losses.

3) It is assumed that the undesirable formation of discoloration in the DMEOA is attributable to complicated decomposition mechanisms (E. Tobler et al., Helv. Chim. Acta 52, 1969, page 408-418) of these quaternary ammonium compounds to give volatile unsaturated compounds, which then polymerize (DD 203 534 A).

What follows is prior art with regard to the preparation of color-stable dialkylethanolamines.

Water-catalyzed processes with specific workup:

EP 70 978 A (Pennwalt Corp.): Continuous reaction of excess DMA (2.2 eq) with EO in the presence of water (0.2-0.5 eq) at 150°; distillative workup with addition of defined amounts of sodium borohydride.

U.S. Pat. No. 3,131,132 A (Jefferson Chem. Comp., Inc.): Batchwise reaction of excess DMA (1-2 eq) with EO in the presence of water (3-15 eq) at 50-100° C.; distillative workup (190 mbar) after adjustment of the pH to 11.5 by addition of acid.

JP 01160947 A (Mitsubishi Gas Chem. Co., Inc.): Water-catalyzed synthesis of DMEOA; workup by distillative high boiler removal (100 mbar); hydrogenation of the distillate over Ru/C; purifying distillation at 100 mbar.

Disadvantages of these processes are the additional material and energy costs resulting from the aftertreatment.

Specific workup or aftertreatment variants:

JP 61186349 A (Daicel Chem. Ind., Ltd.): Distillative workup (200 mbar) of crude DMEOA with addition of urea.

JP 57021351 A (Mitsubishi Gas Chem. Co., Inc.): Hydrogenation of crude DMEOA over $Ru/Al_2O_3$.

EP 28 555 A1 (PCUK Produits Chim. Ugine Kuhlmann): Hydrogenation of crude DMEOA over Raney nickel.

DE 30 40 732 A1 (PCUK Produits Chim. Ugine Kuhlmann): Purification of DMEOA by after-treatment with ammonium salts.

U.S. Pat. No. 6,774,264 B2 (Air Prod. and Chem., Inc.): Hydrogenation of crude DMEOA $Pd/Al_2O_3$.

Disadvantages of these processes too are the additional material and energy costs resulting from the aftertreatment.

Anhydrous processes (T<200° C.):

JP 01157938 A (Mitsubishi Gas Chem. Co., Inc.): Continuous process at 150° C./21 bar; recycling of defined amounts of the reaction output into the reactor (autocatalysis).

DE 23 57 076 A1 (BASF AG): Continuous process; recycling of defined amounts (0.01-0.5 times the amount based on EO plus DMA) of the reactor output (autocatalysis). Color-stable products in reactions <160° C.

Processes with stabilizing additives:

U.S. Pat. No. 3,567,779 A (Jefferson Chem. Comp., Inc.): Inhibition of discoloration by addition of mono- or diethanolamine to give DMEOA.

A disadvantage is that stabilizing additives are undesirable for many applications of N,N-dialkylethanolamines such as DMEOA.

Water-catalyzed processes without aftertreatment:

DD 203 534 A: Reaction of excess DMA (1.1-3.5:1) with EO in the presence of catalytic amounts of water (0.02-0.15 eq) under very mild reaction conditions (50-90° C.); distillative workup with max. still temperature of 90° C.

A disadvantage is that the lowering of the reaction temperature below 90° C. according to the literature (Helv. Chim. Acta 52, 1969, page 408-418) leads to the formation of quaternary bases (→yield losses). Quaternary bases can release acetaldehyde as a result of thermal decomposition in the subsequent workup and lead to poor color stability in the end product.

EP 752 412 A1 (BASF AG) (equivalent DE 44 14 879 A): Reaction of excess DMA with EO in the presence of water (2.5-50% by weight, preferably 8-25% by weight) at reaction temperatures of ≥90° C. and distillative workup at temperatures of max. 90° C.

A disadvantage is that the bottom temperature in the distillative workup has to be kept 90° C.

Water-catalyzed reactions of ethylene oxide with dimethylamine at reaction temperatures of >90° C. are prior art (e.g. EP 70 978 A; DE 44 14 879 A, see above). The color stability of DMEOA produced in such a way, however, has to be ensured either by subsequent treatment of the crude output (for example with a reducing agent/post-hydrogenation (U.S. Pat. No. 6,774,264, see above) or with acids) or by maintaining maximum bottom temperatures (<90° C., DE 44 14 879 A) in the purifying distillation.

DETAILED DESCRIPTION OF THE INVENTION

It was an object of the present invention to overcome disadvantages of the prior art and discover an improved, economically viable process for preparing N,N-dialkylethanolamines, especially DMEOA. The process should be highly selective under operationally reliable working conditions, and give the N,N-dialkylethanolamines having high color stability with a high space-time yield (STY). The process should not require use of any additional assistance (stabilizing additives which inhibit discoloration).

[Space-time yields are reported in 'amount of product/(catalyst volume·time)' (kg/($I_{cat}$·h)) and/or 'amount of product/(reactor volume·time)' (kg/($I_{reactor}$·h)].

Accordingly, a process has been found for preparing an N,N-dialkylethanolamine of the formula I having high color stability

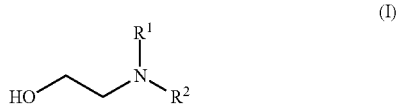

(I)

where $R^1$ and $R^2$ are each independently a $C_1$- to $C_8$-alkyl group, by reacting ethylene oxide (EO) with a corresponding dialkylamine ($R^1R^2NH$) in the presence of water, wherein the reaction is effected continuously in a reactor, the reaction temperature is in the range from 90 to 180° C. and the residence time (RT) in the reactor is in the range from 1 to 7 min, the reactor output is treated thermally at a temperature in the range from 80 to 160° C. over a period in the range from 20 to 1000 min, and then the N,N-dialkylethanolamine is removed by distillation.

$R^1$ and $R^2$ are each independently a linear or branched C1- to C8-alkyl group, preferably $C_1$- to $C_4$-alkyl group. Examples of such alkyl groups are methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl. Particular preference is given to methyl and ethyl.

Particular preference is given to the preparation of N,N-dimethylethanolamine (DMEOA) by reaction of EO with dimethylamine (DMA).

The reaction is effected preferably in the presence of 2.5 to 50% by weight, more preferably 5 to 35% by weight, further preferably 10 to 30% by weight, of water (based on the reaction mixture). In contrast to processes using catalytic amounts of water (0.2-2.0% by weight in DD 203 534 A; DE-C 1 004 620 (Oxirane Ltd.), U.S. Pat. No. 2,823,236 (A. J. Lowe et al.)), this achieves higher reaction rates and higher space-time yields.

The reactants are preferably used in a molar ratio of dialkylamine:EO in the range from 1.1 to 10, more preferably 1.5 to 9, further preferably 3 to 8.

This substantially suppresses the formation of quaternary bases and more highly ethoxylated products, and accordingly achieves a high selectivity.

The reaction is preferably effected in a liquid-cooled tubular reactor.

Particular preference is given to a jacketed reactor. The reactor can be cooled in cocurrent or countercurrent. With regard to product quality (color number, color stability), cocurrent cooling has been found to be advantageous. Therefore, further preferably, the cooling liquid flows in cocurrent through the jacketed reactor.

The reaction is effected preferably at an absolute pressure in the range from 10 to 40 bar, more preferably 15 to 30 bar.

The reaction temperature is preferably in the range from 110 to 170° C., more preferably in the range from 125 to 160° C.

The RT in the reactor is preferably in the range from 2 to 5 min, further preferably in the range from 2 to 4 min.

According to the invention, the reactor output is thermally treated at a temperature in the range from 80 to 160° C., preferably 125 to 155° C., over a period in the range from 20 to 1000 min, preferably 30 to 700 min.

Preferably, the thermal treatment of the reactor output is preceded by distillative removal of unconverted dialkylamine.

The thermal treatment can be effected in a separate vessel (delay vessel) or preferably in the bottom vessel of the dialkylamine distillation column.

The thermal treatment is followed by a distillative workup to remove the N,N-dialkylethanolamine.

After distillative removal and recycling of excess dialkylamine, the water is removed and preferably recycled into the process. The purifying distillation of the N,N-dialkylethanolamine is possible in batchwise mode, but is preferably performed in continuous mode. In the purifying distillation, high boilers (for example more highly ethoxylated products and vinyloxyethanol) are discharged as the bottom product; the N,N-dialkylethanolamine, e.g. the DMEOA, is distilled off either via the top or preferably via a side draw. Low boilers such as alkoxyethanol can be removed via the top in this case.

Particular preference is thus given to distillative N,N-dialkylethanolamine removal in a continuous mode in a side draw column in which the N,N-dialkylethanolamine is obtained in the side draw.

According to the invention, the N,N-dialkylethanolamine of the formula I, e.g. DMEOA, is obtained in 99.00-99.99%, particularly 99.50 to 99.99%, purity.

In particular, the process according to the invention affords the N,N-dialkylethanolamine of the formula I with an APHA color number of ≤15, particularly ≤13, more particularly ≤11, for example in the range from 1 to 10.

In addition, the process according to the invention affords, in particular, the N,N-dialkylethanolamine of the formula I with such a color stability that heating to 60° C. for 24 h under $N_2$ causes an increase in the APHA color number by only 0 to 20%, particularly 0 to 15%.

The APHA color number is determined to DIN-ISO 6271.

The specification of EO used in the process according to the invention is preferably: >99.9% EO, <60 ppm $H_2O$, <50 ppm acetaldehyde, <20 ppm $CO_2$, <20 ppm acetic acid.

The specification of DMA used with preference in the process according to the invention is in particular: >99.5% DMA, <0.1% monomethylamine (MMA), <0.1% $NH_3$, <0.1% MeOH, <0.05% (trimethylamine) TMA, <0.2% $H_2O$.

ppm figures are based on the mass (ppm by mass).

All pressure figures are based on the absolute pressure.

EXAMPLES

Example 1

In a 500 ml tubular reactor with pressure and temperature display, a mixture of dimethylamine (3350 g/h; 74.5 mol/h)

and water (840 g/h; 46.7 mol/h; 21.3% by weight based on the reaction mixture) preheated to 90° C. was reacted continuously with 600 g/h (13.6 mol/h) of ethylene oxide. Owing to the exothermicity of the reactor, a hotspot formed in the reactor. The reactor contents were cooled to 140° C. by external cooling, and it was kept at this temperature optionally by external supply of heat, for 2.4-2.9 min.

After distillative removal and recycling of excess dimethylamine (3 bar/bottom temperature 140° C./RT 35 min) and water (azeotrope with dimethylethanolamine; 400 mbar/bottom temperature 110° C.), 1275 g/h of ethylene oxide-free crude product were obtained with the following composition:
Dimethylethanolamine: 97.0%
Dimethylaminodiglycol: 1.2%
Other products: 1.8%
(Percentages are based on GC analysis. Conditions: 30 m DB1 column with the following temperature program: 75° C.-8° C./min to 280° C.-12 min at 280° C.)
(RT=residence time)

Continuous distillative workup at 50-60 mbar (bottom temperature 70-100° C.) gave dimethylethanolamine in 99.8-99.9% purity with a color number of 5 APHA.
Color number after 24 h/60° C.: 5 APHA,
Color number after 3 months at room temperature under nitrogen: 10 APHA.

Low-boiling secondary components (residual water, methoxyethanol, etc.) were drawn off via the top, high boilers (dimethylaminodiglycol, vinyloxyethanol, etc.) via the bottom, and dimethylethanolamine via a side draw.

The color stability is determined via the following test:
Determination of the color number (APHA) after heating of the DMEA at 60° C. under nitrogen for 24 h.

Example 2

The reaction was conducted as described in Example 1.
Excess dimethylamine was first removed from the reactor output. Compared to Example 1, the RT in the column bottom was 14 min and the bottom temperature 140° C. Thereafter, the column bottoms were conducted into a vessel at 90° C. The RT in the vessel was 660 min. Subsequently, water was removed to obtain 1275 g/h of ethylene oxide-free crude product having a >97% content of dimethylethanolamine.

Continuous distillative workup at 50-60 mbar (bottom temperature 70-100° C.) gave dimethylethanolamine in 99.8-99.9% purity with a color number of 5 APHA.
Color number after 24 h/60° C.: 5 APHA,
Color number after 3 months at room temperature under nitrogen: 10 APHA.

Low-boiling secondary components (residual water, methoxyethanol, etc.) were drawn off via the top, high boilers (dimethylaminodiglycol, vinyloxyethanol, etc.) via the bottom, and dimethylethanolamine via a side draw.
(For determination of color stability see Example 1.)

Comparative Example

The reaction was conducted as described in Example 1.
Excess dimethylamine was first removed from the reactor output. Compared to Example 1, the RT in the column bottom was 14 min and the bottom temperature 140° C. Subsequently, water was removed to obtain 1275 g/h of ethylene oxide-free crude product having a >97% content of dimethylethanolamine.

Continuous purifying distillation at 50-60 mbar (bottom temperature 70-100° C.) gave dimethylethanolamine in 99.8-99.9% purity with a color number of 5 APHA.
Color number after 24 h/60° C.: 50 APHA,
Color number after 3 months at room temperature under nitrogen: 55 APHA.

The dimethylethanolamine product of value was removed via a side draw as described in Example 1. Low-boiling secondary components (residual water, methoxyethanol, etc.) were drawn off via the top, high boilers (dimethylaminodiglycol, vinyloxyethanol, etc.) via the bottom.
(For determination of color stability see Example 1.)

The examples show, more particularly:
The advantages of the process over the prior art lie especially firstly in the high reaction rate, i.e. the process can also be performed economically on the industrial scale. The formation of quaternary ammonium compounds and more highly ethoxylated compounds is minimal under the reaction conditions found, i.e. higher selectivities are achieved compared to reactions in the presence of catalytic amounts of water. When the crude product is worked up under the conditions found, N,N-dialkylethanolamine is obtained, here N,N-dimethylethanolamine, with high color stability, without addition of auxiliary reagents (auxiliaries), without post-hydrogenation and without limitation of the bottom temperature to <90° C. in the purifying distillation.

The invention claimed is:

1. A process for preparing an N,N-dialkylethanolamine of the formula I having high color stability

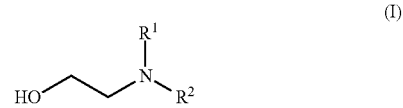

wherein $R^1$ and $R^2$ are each independently a $C_1$- to $C_8$-alkyl group, comprising:
reacting ethylene oxide (EO) with a corresponding dialkylamine ($R^1R^2NH$) in the presence of water, wherein the reaction is effected continuously in a reactor, the reaction temperature is in the range of from 90 to 180° C. and the residence time (RT) in the reactor is in the range of from 1 to 7 min,
and treating the reactor output thermally at a temperature in the range of from 80 to 160° C. over a period in the range of from 20 to 1000 min, and
removing the N,N-dialkylethanolamine from the reactor output by distillation.

2. The process according to claim 1, wherein the thermal treatment of the reactor output is preceded by distillative removal of unconverted dialkylamine in a dialkylamine distillation column.

3. The process according to claim 2, wherein the dialkylamine distillation column comprises a bottoms vessel and the thermal treatment is effected in the bottoms vessel of the dialkylamine distillation column.

4. The process according to claim 1, wherein the reaction temperature is in the range of from 110 to 170° C.

5. The process according to claim 1, wherein the RT in the reactor is in the range of from 2 to 5 min.

6. The process according to claim 1, wherein the reactor output is treated thermally at a temperature in the range of from 125 to 155° C.

7. The process according to claim 1, wherein the reactor output is treated thermally over a period in the range of from 30 to 700 min.

8. A process for preparing an N,N-dialkylethanolamine of the formula I having high color stability

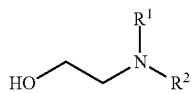 (I)

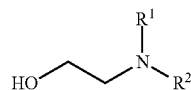 (I)

wherein $R^1$ and $R^2$ are each independently a $C_1$- to $C_8$-alkyl group, comprising:

reacting ethylene oxide (EO) with a corresponding dialkylamine ($R^1R^2NH$) in the presence of water, wherein the reaction is effected continuously in a reactor, the reaction temperature is in the range of from 90 to 180° C. and the residence time (RT) in the reactor is in the range of from 1 to 7 min, and treating the reactor output thermally at a temperature in the range of from 80 to 160° C. over a period in the range of from 20 to 1000 min, and removing the N,N-dialkylethanolamine from the reactor output by distillation, wherein the reactor is a liquid-cooled tubular reactor which utilizes a cooling liquid.

9. The process according to claim 8, wherein the reactor is a jacketed reactor.

10. The process according to claim 9, wherein the cooling liquid flows through the jacketed reactor in cocurrent.

11. The process according to claim 1, wherein the reaction takes place in the presence of 2.5 to 50% by weight of water (based on the reaction mixture).

12. The process according to claim 1, wherein the dialkylamine and the EO are in a molar ratio of dialkylamine:EO in the range of from 1.1 to 10.

13. The process according to claim 1, wherein the reaction is carried out at an absolute pressure in the range of from 10 to 40 bar.

14. A process for preparing an N,N-dialkylethanolamine of the formula I having high color stability wherein $R^1$ and $R^2$ are each independently a $C_1$- to $C_8$-alkyl group, comprising:

reacting ethylene oxide (EO) with a corresponding dialkylamine ($R^1 R^2NH$) in the presence of water, wherein the reaction is effected continuously in a reactor, the reaction temperature is in the range of from 90 to 180° C. and the residence time (RT) in the reactor is in the range of from 1 to 7 min, and treating the reactor output thermally at a temperature in the range of from 80 to 160° C. over a period of from 20 to 1000 min, and removing the N,N-dialkylethanolamine from the reactor output by distillation, wherein the distillative N,N-dialkylethanolamine removal is effected continuously in a side draw column in which the N,N-dialkylethanolamine is obtained in the side draw.

15. The process according to claim 1 wherein the N,N-dialkylethanolamine of the formula I has an APHA color number of ≤15.

16. The process according to claim 1 wherein the N,N-dialkylethanolamine of the formula I has such a color stability that heating to 60° C. for 24 h under N2 causes an increase in the APHA color number by only 0 to 20%.

17. The process according to claim 1 wherein $R^1$ and $R^2$ are each independently a $C_1$- to $C_4$-alkyl group.

18. The process according to claim 1 for preparing N,N-dimethylethanolamine (DMEOA) wherein the corresponding dialkylamine is dimethylamine (DMA).

\* \* \* \* \*